(12) United States Patent
Munson

(10) Patent No.: US 6,770,085 B1
(45) Date of Patent: Aug. 3, 2004

(54) HEAT ABSORBING PAD

(76) Inventor: Ryan R Munson, 11024 Greenaire Dr., Tampa, FL (US) 33624

( * ) Notice: Subject to any disclaimer, the term of this patent is extended or adjusted under 35 U.S.C. 154(b) by 0 days.

(21) Appl. No.: 10/249,471

(22) Filed: Apr. 11, 2003

(51) Int. Cl.$^7$ .................................................. A61F 7/00
(52) U.S. Cl. ........................................ 607/104; 607/96
(58) Field of Search ................................ 607/104, 108

(56) References Cited

U.S. PATENT DOCUMENTS

| | | | | |
|---|---|---|---|---|
| 3,888,259 A | * | 6/1975 | Miley ........................ 607/104 |
| 3,967,627 A | * | 7/1976 | Brown ....................... 607/104 |
| 4,459,468 A | * | 7/1984 | Bailey ....................... 219/490 |
| 4,962,761 A | * | 10/1990 | Golden ...................... 607/104 |
| 5,097,829 A | * | 3/1992 | Quisenberry ............... 607/105 |
| 5,344,436 A | * | 9/1994 | Fontenot et al. ........... 607/104 |
| 5,562,604 A | * | 10/1996 | Yablon et al. .............. 601/148 |
| 5,653,741 A | * | 8/1997 | Grant ........................ 607/114 |
| 5,895,418 A | * | 4/1999 | Saringer .................... 607/104 |
| 2001/0039439 A1 | * | 11/2001 | Elkins et al. ............... 607/104 |
| 2004/0068309 A1 | * | 4/2004 | Edelman .................... 607/104 |

* cited by examiner

Primary Examiner—Lee Cohen
Assistant Examiner—Henry M. Johnson, III

(57) ABSTRACT

A pad whose purpose is to remove heat from a person's body part or pillow. A bladder enclosing a spongy pad and a liquid is where the heat absorbing takes place boiling the liquid in to a vapor. A tube for conveying the vapor to a cooling unit. A cooling unit that condense the vapor back into a liquid using a thermoelectric module to remove the heat.

1 Claim, 3 Drawing Sheets

HEAT ABSORBING PAD

BACKGROUND OF INVENTION

Often times when people have difficulty sleeping it is because they are uncomfortable. Many factors go into determining the comfort level of a person. One of which that is not easily controlled is the temperature of their pillow. If the pillow is not within a comfortable temperature level the person can toss and turn all night trying to get comfortable. People will often times flip their pillow to try to keep it at a lower temperature. This is not an effective method of controlling the temperature of the pillow.

U.S. Pat. No. 4,459,468 to Bailey (1984) shows a device that uses a thermal cooler to control the temperature of a fluid and pump it through a blanket that can be placed on a person. The blanket is designed to be placed on top of a person. It could work in the same manner when placed on top of a pillow and it would be able to control the temperature of the pillow. This device is reliant upon a fluid pump to move the chilled fluid through the blanket.

U.S. Pat. No. 5,097,829 to Quisenberry (1992) is an improvement on the Bailey system in that it will stop the pump and the thermal electric cooler when the system has run out of fluid. This device also uses a pump to move the fluid through the blanket.

U.S. Pat. No. 5,653,741 to Grant (1995) is a flexible pad capable of heating or cooling an animal or human body part. This device uses thermoelectric modules to cool one side of the pad. The pad itself contains the thermoelectric modules and uses air moving through the pad to cool the hot side of the thermoelectric modules.

As with all of the aforementioned devices for cooling, none use a heat pipe as a method of moving heat away from the area being cooled. Heat pipes are generally composed of a tube, closed on each end, with fluid in it. One end takes in heat and the other expels it. The heat entering the "hot" end of the tube boils the liquid which turns it into a vapor. The vapor expands in volume and travels to the "cold" end where it condenses to a liquid and gives up its heat. The fluid is then returned to the hot end by gravity or a wick and starts the process again.

SUMMARY OF INVENTION

The present invention, henceforth known as the cooling pad, is a device for transferring heat away from a persons body part or pillow. The invention provides a flexible bladder for applying under a persons head or under said persons pillow containing a fluid, a tube connected to the bladder for moving fluid or vapor and a thermoelectric driven cooling unit for condensing the vapor. The bladder is a container comprised of an elastomer with good heat transferring properties containing a spongy pad and a fluid with a boiling temperature below room temperature. The tube is a means for the heated fluid or vapor to evacuate the bladder and move up to the cooling unit. The cooling unit removes the heat from the vapor and condenses it back in to a liquid. The cooled liquid is then able to flow back down to the bladder via the tube where the cycle begins again. The spongy pad within the bladder provides added comfort to the user and also acts as a wick to draw in the cooled liquid.

The cooling pad is novel device for providing heat relief without being cold like an icepack. The temperature of the cooling pad remains around room temperature there by providing heat relief without a cold feeling. This is particularly important for people who experience hot flashes. As the hot flash sets in the person heats up, the cooling pad absorbs the additional heat using a phase shift of the fluid to absorb the heat. When the fluid absorbs the heat it boils to become a vapor and evacuates the bladder along with the absorbed heat.

DETAILED DESCRIPTION

Figure 1:
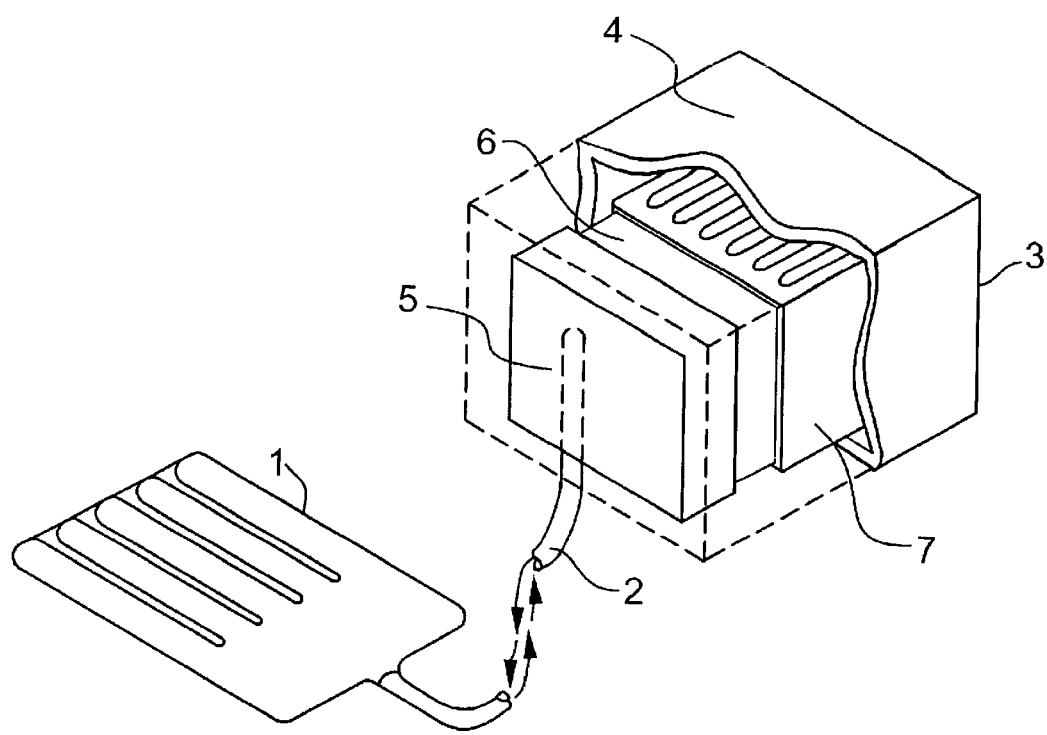
FIG. 1 is a perspective view of the preferred embodiment with the cover partially broken away to show the inner components.
Figure 2:
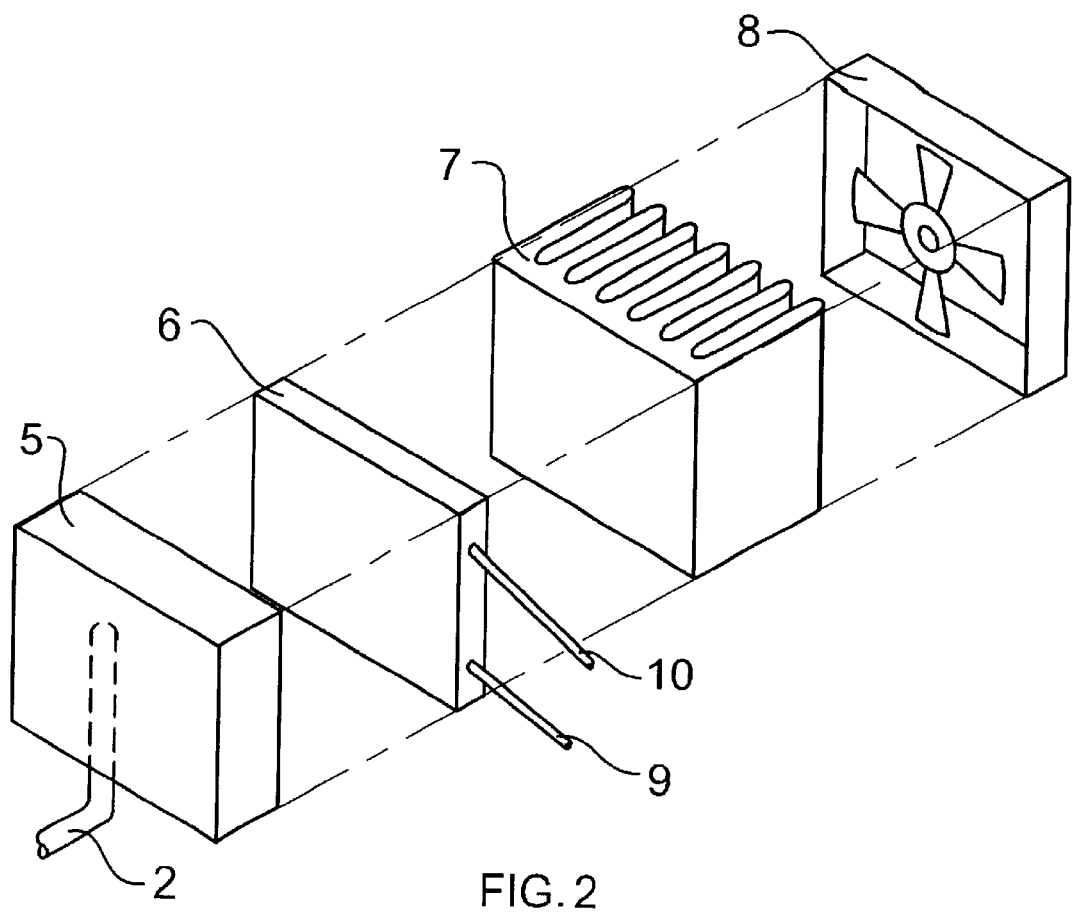
FIG. 2 is an exploded partial perspective view of the cooling unit incorporated in the present invention.

FIG. 1 depicts a perspective view of one preferred embodiment of the present invention. The bladder(1) of this prototype of the present invention is a pad constructed of two butyl rubber sheets sandwiched together and sealed at the edges where heat is absorbed. Enclosed within the bladder is a fluid. In this preferred embodiment the fluid is R-245fa (pentapropane) chosen for if its boiling temperature of just below room temperature at 1 atmosphere of pressure, it's environmentally friendly and non-flammable. Absorbed heat is used to boil the fluid in to a vapor. The vapor is then expelled from the bladder(1) via a tube(2). The tube(2) carries the vapor up to the cooling unit(3) where the vapor enters the condensing block(5). While the vapor is in the condensing block(5) heat (kinetic energy) is removed from the vapor until the vapor is condensed back in to a liquid. The condensed liquid is then able to flow back down the tube(2) to the bladder(1). Heat is removed from the condensing block(5) using a thermoelectric heat pump(6) which has the ability to cool the block below room temperature. The cooling unit(3) expels its heat via a heat sink(7) in to ambient air. An enclosure(4) houses the cooling unit but still allows for free air movement from the surrounding air FIG. 2 is an exploded partial perspective view of the cooling unit incorporated in the present invention giving a more detailed view of the cooling unit then FIG. 1. The condensing block(5) is a block of copper with a hollowed space within it. The hollowed spaces is not open to the atmosphere. It's only open to the tube(2) that brings in the R-245fa vapor. The condensing block(5) is kept at a temperature lower then room temperature via a thermoelectric module(6). The thermoelectric module(6) produces a temperature differential between its hot side and its cold side when electricity is allied to the thermoelectric module's two wire leads(9)(10). The cold side of the thermoelectric(6) is pressed against the condensing block(5) and the hot side is pressed against a heat sink(7). Heat from the thermoelectric (6) is transferred in to the heat sink(7) and dispersed throughout the heat sink(7). A fan(8) blows ambient air on to the heat sink(7). Heat from the heat sink(7) is transferred in to the ambient air which takes the heat away from the present invention.

Figure 3:
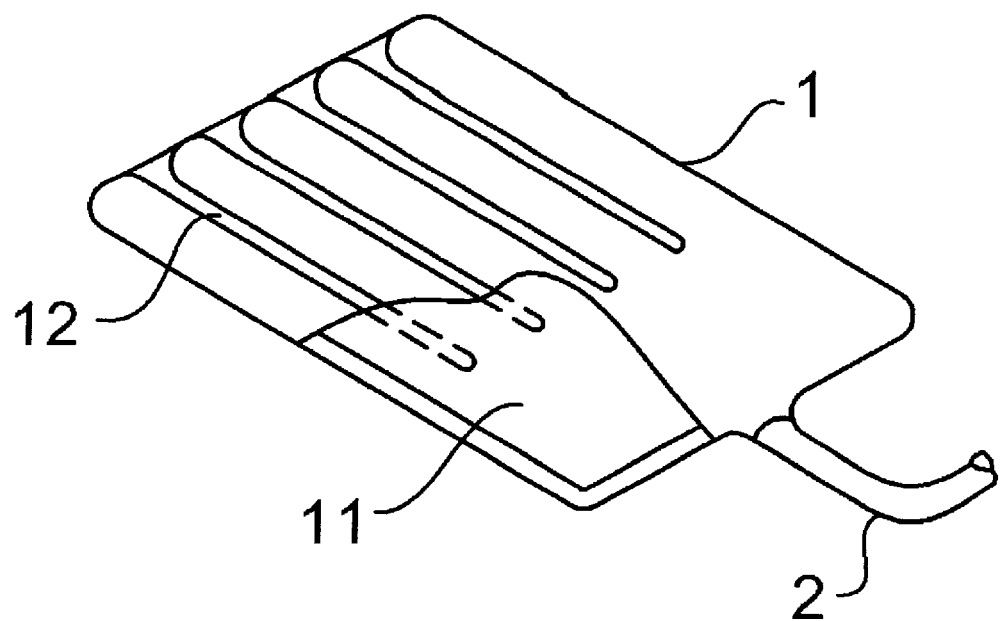
FIG. 3 is a partial perspective view of the heat absorbing bladder incorporated in the present invention with the top layer partially broken away.

FIG. 3 is a partial perspective view of the bladder(1) incorporated in the present invention with the top layer partially broken away. The bladder(1) is comprised of two opposing butyl sheets sealed at the edges with channels(12) to give the pad structure. A spongy pad(11) is contained with in the bladder (1) along with R-245fa liquid. The spongy pad(11) acts as a wick to draw in the liquid R-245fa and to give added comfort to the user. A tube(2) is connected to the bladder(1) to provide a means for the R-245fa vapor to leave the bladder(1) and to allow cooled R-245fa liquid to be drawn back in to the bladder(1).

Many embodiments and variations of the present invention for removing heat from a person's body part or pillow using a heat pipe are possible. However, it should be apparent that the disclosure of the previous embodiment of the present invention will suggest many alternative designs to those skilled in the art. Possible additions or improvements to this design could include but not limited to: adding a pressure control system for regulating the boiling temperature of the fluid or for safety reasons, adding a temperature control system to change the rate of vapor condensation, adding the ability to reverse polarity on the thermoelectric module thus making a pillow warmer, using a different fluid such as R-141b, using a different rubber sheet such as silicone or urethane, adding a displays such as on/off or temperature, adding a timer for turning the device on or off making the cooling pad portable for cooling a person in a suit or in an hot environment.

What is claimed is:

1. A thermal absorbing pad comprising:
    a bladder made of an elastomer material with good heat transfer properties;
    a thermoelectric cooling unit;
    a tube acting as a heat pipe connected to the bladder and in thermal communication with said cooling unit; and
    a fluid with a boiling point lower than room temperature at 1 atmosphere of pressure contained within said bladder and heat pipe.

* * * * *